US010035759B2

(12) United States Patent
Hoke et al.

(10) Patent No.: US 10,035,759 B2
(45) Date of Patent: Jul. 31, 2018

(54) METHOD OF CHROMATOGRAPHIC SEPARATION

(71) Applicant: The Procter & Gamble Company, Cincinnati, OH (US)

(72) Inventors: Steven Hamilton Hoke, West Chester, OH (US); Qingxin Lei, Liberty Township, OH (US); Safa Motlagh, Dayton, OH (US); John Christian Haught, West Chester, OH (US); Michael Reilly, Lebanon, OH (US); Koti Tatachar Sreekrishna, Cincinnati, OH (US); Yakang Lin, Liberty Township, OH (US)

(73) Assignee: THE PROCTER & GAMBLE COMPANY, Cincinnati, OH (US)

( * ) Notice: Subject to any disclaimer, the term of this patent is extended or adjusted under 35 U.S.C. 154(b) by 0 days.

(21) Appl. No.: 15/331,329

(22) Filed: Oct. 21, 2016

(65) Prior Publication Data
US 2017/0036994 A1    Feb. 9, 2017

Related U.S. Application Data (60) Provisional application No. 62/245,189, filed on Oct. 22, 2015.

(51) Int. Cl.
*C07C 261/00* (2006.01)
*C07C 231/24* (2006.01)
*A61K 8/42* (2006.01)
*A61Q 11/00* (2006.01)

(52) U.S. Cl.
CPC .............. *C07C 231/24* (2013.01); *A61K 8/42* (2013.01); *A61Q 11/00* (2013.01); *A61K 2800/244* (2013.01); *C07C 2601/14* (2017.05)

(58) Field of Classification Search
None
See application file for complete search history.

(56) References Cited

U.S. PATENT DOCUMENTS

| | | |
|---|---|---|
| 3,111,127 A | 11/1963 | Jarboe |
| 3,917,613 A | 11/1975 | Humbert et al. |
| 3,991,178 A | 11/1976 | Humbert et al. |
| 4,029,759 A | 6/1977 | Humbert et al. |
| 4,150,052 A | 4/1979 | Watson et al. |
| 4,153,679 A | 5/1979 | Rowsell et al. |
| 4,157,384 A | 6/1979 | Browning et al. |
| 4,136,163 A | 11/1979 | Humbert et al. |
| 4,178,459 A | 12/1979 | Rowsell et al. |
| 4,230,688 A | 10/1980 | Roswell et al. |
| 4,459,425 A | 7/1984 | Amano et al. |
| 5,266,592 A | 11/1993 | Grueb et al. |
| 5,451,404 A | 9/1995 | Furman |
| 5,608,119 A | 3/1997 | Amano et al. |
| 5,703,123 A | 12/1997 | Pelzer et al. |
| 5,725,865 A | 3/1998 | Mane et al. |
| 5,843,466 A | 12/1998 | Mane et al. |
| 5,977,166 A | 11/1999 | Greenberg |
| 6,365,215 B1 | 4/2002 | Grainger et al. |
| 6,451,844 B1 | 9/2002 | Watkins et al. |
| 6,592,884 B2 | 7/2003 | Hofmann et al. |
| 6,884,903 B2 | 4/2005 | Lorenz et al. |
| 6,956,139 B2 | 10/2005 | Green et al. |
| 7,189,760 B2 | 3/2007 | Erman et al. |
| 2008/0255185 A1 | 10/2008 | Moreno et al. |
| 2010/0086498 A1 | 4/2010 | Haught et al. |

FOREIGN PATENT DOCUMENTS

| | | |
|---|---|---|
| EP | 310299 | 4/1989 |
| GB | 1315626 | 5/1973 |
| WO | WO2005049553 | 6/2005 |
| WO | WO2006103401 | 10/2006 |
| WO | WO2009067410 | 5/2009 |
| WO | WO2010019730 | 2/2010 |
| WO | WO2015/164553 | * 10/2015 |

OTHER PUBLICATIONS

International Search Report with Written Opinion dated Jan. 18, 2017, 11 pages.
Synthesis and Sensory Characterization of Menthol Enantiomers and Their Derivatives for the Use in Nature Identical Peppermint Oils, R. Emberger and R. Hopp, Specialty Chemicals (1987), 7(3), 193-201).
AG-3-5: A Chemical Producing Sensations of Cold, E. T. Wei, D. A. Seid, J. Pharm. Pharmacol. (1983), 35:110-112.
New Compounds With The Menthol Cooling Effect, H. R. Watson, R. Hems, D. G. Rowsell, and D. J. Spring, J. Soc. Cosmet. Chem. (1978), 29, 185-200.
Menthol and Related Cooling Compounds, R. Eccles, J. Pharm. Pharmacol., (1994), 46, 618-630.

* cited by examiner

*Primary Examiner* — Yevegeny Valenrod
*Assistant Examiner* — Blaine G Doletski
(74) *Attorney, Agent, or Firm* — James E. Ochlenschlager (57) ABSTRACT

A means of isolating specific stereoisomers and enantiomers from a complex mixture containing a possibility of 32 different stereoconfigurations, thus concentrating the stereoisomer or enantiomer to a high degree of purity.

16 Claims, 3 Drawing Sheets

METHOD OF CHROMATOGRAPHIC SEPARATION

FIELD OF THE INVENTION

The present invention relates to methods of chromatographic separation from the synthesis of a compound that comprises stereoisomers.

BACKGROUND OF THE INVENTION

Oral care products, such as dentifrice and mouthwash, are routinely used by consumers as part of their oral care hygiene regimens. It is well known that oral care products can provide both therapeutic and cosmetic hygiene benefits to consumers. Therapeutic benefits include caries prevention which is typically delivered through the use of various fluoride salts; gingivitis prevention, by the use of an antimicrobial agent such as stannous fluoride, triclosan, essential oils; or hypersensitivity control through the use of ingredients such as strontium chloride or potassium nitrate. Cosmetic benefits provided by oral care products include the control of plaque and calculus formation, removal and prevention of tooth stain, tooth whitening, breath freshening, and overall improvements in mouth feel impression, which can be broadly characterized as mouth feel aesthetics. Calculus and plaque along with behavioral and environmental factors lead to formation of dental stains, significantly affecting the aesthetic appearance of teeth. Behavioral and environmental factors that contribute to teeth staining propensity include regular use of coffee, tea, cola or tobacco products, and also the use of certain oral products containing ingredients that promote staining, such as cationic antimicrobials and metal salts.

Thus daily oral care at home requires products with multiple ingredients working by different mechanisms to provide the complete range of therapeutic and aesthetic benefits, including anticaries, antimicrobial, antigingivitis, antiplaque, anticalculus and anti-erosion, as well as anti-odor, mouth refreshment, stain removal, stain control and tooth whitening. In order for daily use oral care products, such as dentifrice and rinses to provide complete oral care it is often necessary to combine actives and additives, many of which have the disadvantage of causing negative aesthetics during use, in particular unpleasant taste and sensations and stain promotion. The unpleasant taste and mouth sensations have been described as having one or more of bitter, metallic, astringent, salty, numbing, stinging, burning, or prickling, and even irritating aspects. Typical ingredients for oral care use that are associated with these aesthetic negatives include antimicrobial agents such as cetyl pyridinium chloride, chlorhexidine, stannous and zinc salts; tooth bleaching agents such as peroxides; antitartar agents such as pyrophosphate, tripolyphosphate and hexametaphosphate; and excipients such as baking soda and surfactants. To mitigate the aesthetic negatives from these ingredients, oral care products are typically formulated with flavoring agents, sweeteners and coolants to taste as good as possible and provide a pleasant experience. In particular, it is desirable for oral care products to provide a refreshing cooling sensation during and after use. In addition to mitigation of negative sensations, sensate molecules are formulated into oral care compositions to convey a signal of efficacy. Such signals of efficacy include cooling, tingling, numbing, warming, sweetness, and rheological sensations such as phase change and fizzing or bubbling.

A large number of coolant compounds of natural or synthetic origin have been described. The most well-known compound is menthol, particularly 1-menthol, which is found naturally in peppermint oil, notably of *Mentha arvensis* L and *Mentha viridis* L. Of the menthol isomers, the 1-isomer occurs most widely in nature, and is typically what is referred by the name menthol having coolant properties. L-menthol has the characteristic peppermint odor, has a clean fresh taste and exerts a cooling sensation when applied to the skin and mucosal surfaces. Other isomers of menthol (neomenthol, isomenthol and neoisomenthol) have somewhat similar, but not identical odor and taste, i.e., some having disagreeable notes described as earthy, camphor, musty. The principal difference among the isomers is in their cooling potency. L-menthol provides the most potent cooling, i.e., having the lowest cooling threshold of about 800 ppb, i.e., the concentration where the cooling effect could be clearly recognized. At this level, there is no cooling effect for the other isomers. For example, d-neomenthol is reported to have a cooling threshold of about 25,000 ppb and 1-neomenthol about 3,000 ppb. (R. Emberger and R. Hopp, "Synthesis and Sensory Characterization of Menthol Enantiomers and Their Derivatives for the Use in Nature Identical Peppermint Oils," Specialty Chemicals (1987), 7(3), 193-201). This study demonstrated the outstanding sensory properties of 1-menthol in terms of cooling and freshness and the influence of stereochemistry on the activity of these molecules.

Among synthetic coolants, many are derivatives of or are structurally related to menthol, i.e., containing the cyclohexane moiety, and derivatized with functional groups including carboxamide, ketal, ester, ether and alcohol. Examples include the ρ-menthanecarboxamide compounds, such as N-ethyl-ρ-menthan-3-carboxamide, known commercially as "WS-3", and others in the series, such as WS-5 (N-ethoxycarbonylmethyl-ρ-menthan-3-carboxamide), WS-12 [N-(4-methoxyphenyl)-ρ-menthan-3-carboxamide] and WS-14 (N-tert-butyl-ρ-menthan-3-carboxamide). Examples of menthane carboxy esters include WS-4 and WS-30. An example of a synthetic carboxamide coolant that is structurally unrelated to menthol is N,2,3-trimethyl-2-isopropylbutanamide, known as "WS-23". Additional examples of synthetic coolants include alcohol derivatives such as 3-(1-menthoxy)-propane-1,2-diol known as TK-10, isopulegol (under the tradename Coolact P) and ρ-menthane-3,8-diol (under the tradename Coolact 38D); menthone glycerol acetal known as MGA; menthyl esters such as menthyl acetate, menthyl acetoacetate, menthyl lactate known as Frescolat® supplied by Haarmann and Reimer, and monomenthyl succinate under the tradename Physcool from V. Mane. TK-10 is described in U.S. Pat. No. 4,459,425. Other alcohol and ether derivatives of menthol are described e.g., in GB 1,315,626 and in U.S. Pat. Nos. 4,029,759; 5,608,119; and 6,956,139. WS-3 and other carboxamide cooling agents are described for example in U.S. Pat. Nos. 4,136,163; 4,150,052; 4,153,679; 4,157,384; 4,178,459 and 4,230,688. Additional N-substituted ρ-menthane carboxamides are described in WO 2005/049553A1 including N-(4-cyanomethylphenyl)-ρ-menthanecarboxamide, N-(4-sulfamoylphenyl)-ρ-menthanecarboxamide, N-(4-cyanophenyl)-ρ-menthanecarboxamide, N-(4-acetylphenyl)-ρ-menthanecarboxamide, N-(4-hydroxymethylphenyl)-ρ-menthanecarboxamide and N-(3-hydroxy-4-methoxyphenyl)-ρ-menthanecarboxamide. Other N-substituted ρ-menthane carboxamides include amino acid derivatives such as those disclosed in WO 2006/103401 and in U.S. Pat. Nos. 4,136,163; 4,178,459 and

7,189,760 such as N-((5-methyl-2-(1-methylethyl)cyclo-hexyl)carbonyl)glycine ethyl ester and N-((5-methyl-2-(1-methylethyl)cyclohexyl)carbonyl)alanine ethyl ester. Menthyl esters including those of amino acids such as glycine and alanine are disclosed e.g., in EP 310 299 and in U.S. Pat. Nos. 3,111,127; 3,917,613; 3,991,178; 5,703,123; 5,725,865; 5,843,466; 6,365,215; 6,451,844; and 6,884,903. Ketal derivatives are described, e.g., in U.S. Pat. Nos. 5,266,592; 5,977,166 and 5,451,404. Additional agents that are structurally unrelated to menthol but have been reported to have a similar physiological cooling effect include alpha-keto enamine derivatives described in U.S. Pat. No. 6,592,884 including 3-methyl-2-(1-pyrrolidinyl)-2-cyclopenten-1-one (3-MPC), 5-methyl-2-(1-pyrrolidinyl)-2-cyclopenten-1-one (5-MPC), and 2,5-dimethyl-4-(1-pyrrolidinyl)-3(2H)-furanone (DMPF); icilin (also known as AG-3-5, chemical name 1-[2-hydroxyphenyl]-4-[2-nitrophenyl]-1,2,3,6-tetrahydro-pyrimidine-2-one) described in Wei et al., J. Pharm. Pharmacol. (1983), 35:110-112. Reviews on the coolant activity of menthol and synthetic coolants include H. R. Watson, et al. J. Soc. Cosmet. Chem. (1978), 29, 185-200 and R. Eccles, J. Pharm. Pharmacol., (1994), 46, 618-630.

Structures built off of the cyclohexanecarboxamide backbone have been applied as anti-cancer agents as disclosed in WO 2009/067410. As shown in U.S. Pat. No. 4,150,052, only a select few of the cyclohexanecarboxamide derivatives had noticeable cooling. The molecules disclosed in WO 2009/067410 were evaluated for their TRPM8 activity in relation to the destruction of prostate cancer cells; however activating TRPM8 does not necessarily mean that a cooling sensation will be observed. Thus cooling would have been an undesirable effect and something they would have avoided.

The present invention provides methods for separating one or more compositions having coolant properties, wherein the cooling and refreshing sensation provided by the coolant(s) is optimized in terms of onset, intensity, or duration.

SUMMARY OF THE INVENTION

A method of chromatographic separation from the synthesis of a compound is provided that comprises stereoisomers of following structure:

$R_1$ is selected from H, alkyl, amino alkyl, alkoxy;
Q=$H_2$, O, —$OR_1$, —$N(R_1)_2$, —$OPO(OR_1)_x$, —$PO(OR_1)_x$, —$P(OR_1)_x$ where x=1–2;
V=$NR_1$, O, —$OPO(OR_1)_x$, —$PO(OR_1)_x$, —$P(OR_1)_x$ where x=1–2;
W=$H_2$, O;
X, Y=independently selected from H, aryl, naphthyl for n=0;
X, Y=aliphatic $CH_2$ or aromatic CH for n≥1 and Z is selected from aliphatic $CH_2$, aromatic CH, or heteroatom;
A=lower alkoxy, lower alkylthio, aryl, substituted aryl or fused aryl; and
stereochemistry is variable at the positions marked*, and can even vary at the positions marked (S) and (R).

A representation of a compound that can be separated using the methods of the present invention is illustrated below:

where the variable stereochemistry at position #1, when R1 is an alkyl group, is either L or D; the stereochemistry position at position #2 is in the S- or R-position; and the stereochemistry from the menthyl moiety at position #3 is in the L or in the neo-configuration. Positions 4 and 5 are typically in the S and R configurations, respectively, although they may also vary.

This structure, which includes a stereoisomer called compound 28, where R1=$CH_3$, represents a genus that has been surprisingly found to be useful as modulators of TRPM8 activation. A number of stereoisomers are contemplated with these structures, including compound 28, where relative configuration of each stereo center will dictate the activity towards the receptor. In some cases, isomers of the same molecule may have comparable activity. In other cases, stereoisomers of the same molecule could have enhanced or diminished activity towards the receptor. In some cases, individual stereoisomers may have no activity.

These and other features, aspects, and advantages of the present invention will become evident to those skilled in the art from the detailed description that follows.

DETAILED DESCRIPTION OF THE INVENTION

The present invention provides a means of isolating specific stereoisomers from a complex mixture containing a possibility of 32 different stereoconfigurations, thus concentrating the stereoisomer to a high degree of purity. The separation is achieved using a combination of Chiralpak AS-H and AD-H columns.

In certain embodiments the invention provides a mobile phase consisting of carbon dioxide, ethanol, and/or ammonium acetate.

In certain embodiments the invention includes the application of a gradient separation in a supercritical, subcritical or enhanced fluidity stream of pressurized $CO_2$.

In further embodiments the invention includes the application of sequential separations to increase purity of individual isomer to greater than about 70%, greater than about 85%, greater than about 90%, greater than about 95%, greater than about 97%, or greater than about 99% isomerically pure.

All percentages and ratios used hereinafter are by weight of total composition, unless otherwise indicated. All percentages, ratios, and levels of ingredients referred to herein are based on the actual amount of the ingredient, and do not include solvents, fillers, or other materials with which the ingredient may be combined as a commercially available product, unless otherwise indicated.

All measurements referred to herein are made at 25° C. unless otherwise specified.

As used herein, the word "or" when used as a connector of two or more elements is meant to include the elements individually and in combination; for example X or Y, means X or Y or both.

By "personal care composition" is meant a product, which in the ordinary course of usage is applied to or contacted with a body surface to provide a beneficial effect. Body surface includes skin, for example dermal or mucosal; body surface also includes structures associated with the body surface for example hair, teeth, or nails. Examples of personal care compositions include a product applied to a human body for improving appearance, cleansing, and odor control or general aesthetics. Non-limiting examples of personal care compositions include oral care compositions, such as, dentifrice, mouth rinse, mousse, foam, mouth spray, lozenge, chewable tablet, chewing gum, tooth whitening strips, floss and floss coatings, breath freshening dissolvable strips, denture care product, denture adhesive product; after shave gels and creams, pre-shave preparations, shaving gels, creams, or foams, moisturizers and lotions; cough and cold compositions, gels, gel caps, and throat sprays; leave-on skin lotions and creams, shampoos, body washes, body rubs, such as Vicks Vaporub; hair conditioners, hair dyeing and bleaching compositions, mousses, shower gels, bar soaps, antiperspirants, deodorants, depilatories, lipsticks, foundations, mascara, sunless tanners and sunscreen lotions; feminine care compositions, such as lotions and lotion compositions directed towards absorbent articles; baby care compositions directed towards absorbent or disposable articles; and oral cleaning compositions for animals, such as dogs and cats.

The present invention is also directed towards "oral health compositions" as used herein refers to compositions in a form that is deliverable to a mammal in need via the oral cavity, mouth, throat, nasal passage or combinations thereof. Nonlimiting examples include liquid compositions, cough syrups, respiratory preparations, beverage, supplemental water, pills, soft gels, tablets, capsules, gel compositions, foam compositions, saline wash and combinations thereof. Liquid compositions, gel compositions can be in a form that is directly deliverable to the mouth and throat. These compositions and/or preparations can be delivered by a delivery device selected from droppers, pump, sprayers, liquid dropper, saline wash delivered via nasal passageway, cup, bottle, liquid filled gel, liquid filled gummy, center filled gum, chews, films, center filled lozenge, gum filled lozenge, pressurized sprayers, atomizers, air inhalation devices, liquid filled compressed tablet, liquid filled gelatin capsule, liquid filled capsule, squeezable sachets, power shots, and other packaging and equipment, and combinations thereof. The sprayer, atomizer, and air inhalation devices can be associated with a battery or electric power source.

The term "dentifrice", as used herein, includes tooth or subgingival-paste, gel, or liquid formulations unless otherwise specified. The dentifrice composition may be a single phase composition or may be a combination of two or more separate dentifrice compositions. The dentifrice composition may be in any desired form, such as deep striped, surface striped, multilayered, having a gel surrounding a paste, or any combination thereof. Each dentifrice composition in a dentifrice comprising two or more separate dentifrice compositions may be contained in a physically separated compartment of a dispenser and dispensed side-by-side.

The term "dispenser", as used herein, means any pump, tube, or container suitable for dispensing compositions such as dentifrices.

The term "teeth", as used herein, refers to natural teeth as well as artificial teeth or dental prosthesis.

The term "orally acceptable carrier or excipients" includes safe and effective materials and conventional additives used in oral care compositions including but not limited to fluoride ion sources, anti-calculus or anti-tartar agents, buffers, abrasives such as silica, alkali metal bicarbonate salts, thickening materials, humectants, water, surfactants, titanium dioxide, flavorants, sweetening agents, xylitol, coloring agents, and mixtures thereof.

Herein, the terms "tartar" and "calculus" are used interchangeably and refer to mineralized dental plaque biofilms.

| SEQ ID NO | Sequence |
|---|---|
| 1 | Human TRPM8 DNA sequence |

A sequence listing that sets forth the nucleotide sequences for SEQ ID NO: 1 herein is being filed concurrently with the present application as an ASCII text file titled "14075M_Nucleotide_Sequence_Listing_ST25." The ASCII text file was created on 21 Oct. 2016 and is 5 Kbytes in size. In accordance with MPEP §605.08 and 37 CFR § 1.52(e), the subject matter in the ASCII text file is incorporated herein by reference.

The term "TRPM8" or "TRPM8 receptor", as used herein, refers to cold- and menthol-sensitive receptor (CMR1) or TRPM8. The TRPM8 nomenclature for the receptor comes from its characterization as a non-selective cation channel of the transient receptor potential (TRP) family that is activated by stimuli including low temperatures, menthol and other chemical coolants. The TRPM8 receptor is provided as SEQ ID NO: 1.

The cooling receptor conventionally known as TRPM8 or the menthol receptor has been demonstrated as a means to differentiate intensity and duration of organic molecules that initiate and propagate the non-thermal cooling perception (D. D. Mckemy, *The Open Drug Discovery Journal* 2:81-88 2010). McKemy reported the EC50 values of many agonists to TRPM8 which span the range of 100 nM to 19 mM, thus showing the channel can be activated across a wide range of structures at varying concentrations. This channel also has the nomenclature of CRM1 and TRPP8. The latter was designated as such due to its identification with prostate cells, where it was employed as a means to identify molecules targeted towards prostate cancer.

The term "TRPM8 agonist", as used herein, refers to any compound, which when added to a TRPM8 receptor, according to the FLIPR method, as discussed herein, produces any increase in fluorescence over background.

The term "TRPV1" or "TRPV1 receptor", as used herein, refers to the transient receptor potential vanilloid receptor 1, which is a ligand-gated, non-selective cation channel preferentially expressed on small-diameter sensory neurons and detects noxious as well as other substances. The TRPV1 receptor is provided as SEQ ID NO: 1. The TRPV1 receptor responds to, for example, both noxious and painful stimuli. A noxious stimulus would include those that give a burning (i.e. hot) sensation.

The term "TRPV1 agonist", as used herein, refers to any compound, which at a concentration of 1 mM gives a calcium flux count of at least 1000 counts or 20% above the background level of calcium present in the cell according to the FLIPR method, as discussed herein. The term "count" is defined as the change in fluorescence of the cell lines due to the influx of calcium across the cell membrane, which reacts with the calcium sensitive dye present within the cells.

The term "TRPA1" or "TRPA1 receptor", as used herein, refers to the transient receptor potential cation channel, subfamily A, member 1, having a large cysteine-rich N-terminus that contains 18 predicted ankyrin repeats. The TRPA1 receptor is provided as SEQ ID NO: 2. TRPA1 is a ligand-gated, non-selective cation channel preferentially expressed on small diameter sensory neurons. The term "TRPA1 agonist", as used herein, refers to any compound, which at a concentration of 1 mM gives a calcium flux count of at least 1000 counts or 20% above the background level of calcium present in the cell according to the FLIPR method, as discussed herein. The term "count" is defined as the change in fluorescence of the cell lines due to the influx of calcium across the cell membrane, which reacts with the calcium sensitive dye present within the cells.

The term potency, as defined by the Merck Manual, refers to the concentration (EC50) or dose (ED50) of a chemistry required to produce 50% of the chemistry's maximal effect as depicted by a graded dose-response curve. EC50 equals Kd (Dissociation constant, which is a measure of 50% of the substance in question bound to the receptor) when there is a linear relationship between occupancy and response. Often, signal amplification occurs between receptor occupancy and response, which results in the EC50 for response being much less (i.e., positioned to the left on the abscissa of the log dose-response curve) than KD for receptor occupancy. Potency depends on both the affinity of chemistry for its receptor, and the efficiency with which chemistry-receptor interaction is coupled to response. The dose of chemistry required to produce an effect is inversely related to potency. In general, low potency is important only if it results in a need to administer the chemistry in large doses that are impractical. Quantal dose-response curves provide information on the potency of chemistry that is different from the information derived from graded dose-response curves. In a quantal dose-response relationship, the ED50 is the dose at which 50% of individuals exhibit the specified quantal effect.

Coolants or compounds that have a physiological cooling effect particularly on oral and other mucosal surfaces and skin are common ingredients in a wide variety of products, including edible compositions, personal care compositions, and in flavor or perfume compositions. Examples of edible compositions include confectionery, candies, chocolate, chewing gum, beverages and oral medicines. Personal care compositions, including oral care compositions, have been described previously. The pleasant cooling sensation provided by coolants contributes to the appeal and acceptability of the products. In particular, oral care products, such as dentifrices and mouthwashes are formulated with coolants because they provide breath freshening effects and a clean, cool, fresh feeling in the mouth.

It is now well established that sensations such as cool or cold can be attributed to activation of receptors at peripheral nerve fibers by a stimulus such as low temperature or a chemical coolant, which produces electrochemical signals that travel to the brain, which then interprets, organizes and integrates the incoming signals into a perception or sensation. Different classes of receptors have been implicated in sensing cold temperatures or chemical coolant stimuli at mammalian sensory nerve fibers. Among these receptors, a major candidate involved in sensing cold has been identified and designated as cold- and menthol-sensitive receptor (CMR1) or TRPM8. The TRPM8 nomenclature for the receptor comes from its characterization as a non-selective cation channel of the transient receptor potential (TRP) family, which is activated by stimuli including low temperatures, menthol and other chemical coolants. However, the precise mechanisms underlying the perception of a pleasant cooling sensation on skin or oral surfaces are presently not clearly understood. While it has been demonstrated that the TRPM8 receptor is activated by menthol and other coolants, it is not fully understood what other receptors may be involved, and to what extent these receptors need to be stimulated or perhaps suppressed in order for the overall perceived sensation to be pleasant, cooling and refreshing. For example, menthol is widely used as a cooling agent, but menthol can also produce other sensations including tingling, burning, prickling and stinging as well as a minty smell and bitter taste. Thus, it can be inferred that menthol acts on many different receptors, including cold, warm, pain and taste receptors.

Examples of solvents that can be used to solubilize compounds of the present invention, such as compound 28, as discussed below, are based upon solubility parameters and cohesion properties explained by Charles Hansen in "Hansen Solubility Parameters: A User's Handbook" by Charles M. Hansen, CRC Press (2007) and in "The CRC Handbook and Solubility Parameters and Cohesion Parameters," Edited by Allan F. M. Barton (1999). Each material is defined by three points in 3D space and these three points are known as the Hansen Solubility Parameters (HSP) which may be defined as follows.

Solubility parameters are theoretically calculated numerical constants, which are a useful tool in predicting the ability of a solvent material to dissolve a particular solute. When the solubility parameters of a solvent falls within the solubility parameter range of a solute, i.e., the material to be dissolved, solubilization of the solute is likely to occur. There are three Hansen empirically and theoretically derived solubility parameters, a dispersion-force component ($\delta_D$), a polar or dipole interaction component ($\delta_P$) and a hydrogen-bonding component ($\delta_H$). Each of the three parameters (dispersion, polar and hydrogen bonding) represents a different characteristic of solvency, or solvent capability. In combination, the three parameters are a measure of the overall strength and selectivity of a solvent. The Total Hansen solubility parameter, which is the square root of the sum of the squares of the three parameters mentioned previously, provides a more general description of the solvency of the solvents. Individual and total Solubility Parameter units are given in $MPa^{0.5}$. Solubility parameters for a material may then be plotted in a normal three-dimensional graph. From the location ($\delta_D$, $\delta_P$, $\delta_H$), a radius is projected to form a sphere, which encompasses a region of solubility such that any solvent whose parameters reside within this space should dissolve the solute in question. The distance between the HSP coordinate of material (i.e., the solute) to the HSP coordinates of material (solvent) is designated herein as Ra. The 3D distance, Ra, is defined by the equation: $Ra^2=4(\delta_{D1}-\delta_{D2})^2+(\delta_{P1}-\delta_{P2})^2+(\delta_{H1}-\delta_{H2})^2$ The sphere equation of Hansen was calculated to center the target molecules of choice, in this case, compound 28 and the various isomers (L, D, and neo) and enantiomers of each. The target Polar, Dispersive, and Hydrogen Bonding HSP are the Hansen solubility parameters of the target molecule as calculated by "Molecular Modeling Pro" software, version 5.1.9 (ChemSW, Fairfield Calif., www.chemsw.com) or Hansen Solubility from Dynacomp Software. The solubility parameters of every solvent in this analysis were also calculated via this software. Within the sphere having a radius $R_a=14$ are solvents into which compound 28 and isomer materials will be soluble. For solubility >5% in the selected solvents, the preferred range of $\delta_{dispersion}$ is ±3 units, from about 15.2 to 21.2 $(MPa)^{0.5}$. The preferred range of $\delta_{polarity}$ is ±6 units, from about 0 to 10.8 $(MPa)^{0.5}$. The preferred range of $\delta_{Hydrogen}$ bonding is ±13 units, from about 0 to 25 $(MPa)^5$. The HSP of compound 28 were calculated as dispersion=17.8, polarity=5.6, and hydrogen bonding=9.0. Non-limiting examples of flavor and fragrance raw materials having suitable Hansen Solubility Parameters used to solubilize the carboxamide derivative (compound 28) include menthone, carvone, pine oil, cinnamic aldehyde, ethanol, benzyl alcohol, eucalyptol, 1,2-propane diol, 1,3-propane diol, hexane, ethanolamine, cyclodextrins, and triacetin.

Ideally, a coolant can produce a cooling or freshness sensation similar to that produced by menthol, but without certain of the disadvantages associated with menthol, such as flavor modification, bitter aftertaste, off-flavor, strong odor and burning or irritating sensation, particularly at high concentrations. It is desirable that the coolant compounds barely possess a distinctive odor or flavor while providing a pleasant fresh cool sensation of prolonged duration, in order that the effect can still be perceived for a considerable time after use, for example, longer than 15 minutes. Menthol generally provides an initial high cooling impact, but its effect is somewhat transient in that the cool sensation drops sharply within a few minutes after use. By contrast, a number of longer lasting coolant compounds may fail to provide an immediate cooling perception, i.e., within a few seconds of application, particularly when used at low levels. Thus there is a continuing need for means to potentiate the activity of coolant chemicals, in terms of quickening the onset of the cooling sensation, intensifying the cooling sensation, especially at lower concentrations, and producing a longer lasting sensation of cooling and freshness than what menthol provides.

As stated previously, the present invention is directed to one or more methods of isolating specific stereoisomers from 5-methyl-2-(1-methylethyl)-N-(2-phenylethyl)-, (1R, 2S,5R) cyclohexanecarboxamide structures, as shown below, which can drive a cooling response at low concentrations.

Structure I, which includes compound 28, represents a genus that has been surprisingly found to be useful as modulators of TRPM8 activation. Structure I represents a heteroalkyl substituted aryl or heteroalkyl-aryl substituted alkyl carboxamide of methanol having the shown below structure and including any acceptable salts or solvates thereof; wherein:

Structure I $R_1$ is selected from H, alkyl, amino alkyl, alkoxy;
$Q=H_2$, O, —$OR_1$, —$N(R_1)_2$, —$OPO(OR_1)_x$, —$PO(OR_1)_x$, —$P(OR_1)_x$ where x=1–2;
$V=NR_1$, O, —$OPO(OR_1)_x$, —$PO(OR_1)_x$, —$P(OR_1)_x$ where x=1–2;
$W=H_2$, O;
X, Y=independently selected from H, aryl, naphthyl for n=0;
X, Y=aliphatic $CH_2$ or aromatic CH for n≥1 and Z is selected from aliphatic $CH_2$, aromatic CH, or heteroatom;
A=lower alkoxy, lower alkylthio, aryl, substituted aryl or fused aryl; and
stereochemistry is variable at the positions marked*, and can even vary at the positions marked (S) and (R).

A number of stereoisomers are contemplated in the above Structure I and can be isolated according to the object of the invention, where substitution is allowed and the relative configuration of each stereo center will dictate the activity towards the receptor. The stereochemistry of side chain groups may be important to the activity of the molecule, however the activity of these compounds in vivo is highly unpredictable. In some cases, isomers of the same molecule may have comparable activity. In other cases, stereoisomers of the same molecule could have enhanced or diminished activity towards the receptor. In some cases, individual stereoisomers may have no activity.

Specific compounds of interest may derive from the 1R, 2S, 5R configuration (shown below in Structure IA) found in natural (−)-menthol. In these cases, the stereoisomeric derivatives of 1R, 2S, 5R-menthyl carboxamide will be found in the substituted alkyl side chain fragment of the molecule. While the 1R, 2S, 5R configuration is important to activity, the 1S, 2S, 5R neo-isomer (shown below in Structure IB) of N-substituted menthyl carboxamide derivatives has also shown promise.

Structure IA

Structure IB

Neo-isomer:

$R_1$ is selected from H, alkyl, amino alkyl, alkoxy;
$Q=H_2$, O, $-OR_1$, $-N(R_1)_2$, $-OPO(OR_1)_x$, $-PO(OR_1)_x$, $-P(OR_1)_x$ where $x=1-2$;
$V=NR_1$, O, $-OPO(OR_1)_x$, $-PO(OR_1)_x$, $-P(OR_1)_x$ where $x=1-2$;
$W=H_2$, O;
X, Y=independently selected from H, aryl, naphthyl for $n=0$;
X, Y=aliphatic $CH_2$ or aromatic CH for $n \geq 1$ and Z is selected from aliphatic $CH_2$, aromatic CH, or heteroatom;
A=lower alkoxy, lower alkylthio, aryl, substituted aryl or fused aryl; and
stereochemistry is variable at the positions marked*, and can even vary at the positions marked (S) and (R).

Examples of some of the stereoisomers that can be separated using the methods of the present invention are listed below.

28

(1R,2S,5R)-N-(2-((R)-2-aminopropanamido)-2-phenylethyl)-2-isopropyl-5-methylcyclohexane-1-carboxamide -continued (1R,2S,5R)-N-((R)-2-aminopropanamido)-2-phenylethyl)-2-isopropyl-5-methylcyclohexane-1-carboxamide

DRL STEREOISOMER (1R,2S,5R)-N-((S)-2-((R)-2-aminopropanamido)-2-phenylethyl)-2-isopropyl-5-methylcyclohexane-1-carboxamide

DSL STEREOISOMER (1R,2S,5R)-N-((S)-2-((S)-2-aminopropanamido)-2-phenylethyl)-2-isopropyl-5-methylcyclohexane-1-carboxamide

LSL STEREOISOMER

It has been discovered that cyclohexanecarboxamide, 5-methyl-2-(1-methylethyl)-N-(2-phenylethyl)-, (1R,2S,5R) (CAS#824947-52-6) and cyclohexanecarboxamide, 5-methyl-2-(1-methylethyl)-N-(2-phenylethyl)-, (1R,2S,5R) (CAS#847564-71-0) structures (shown above) with 2-amino-propanamide (CAS#4726-84-5) have enhanced long lasting cooling properties and cyclohexanecarboxamide, 5-methyl-2-(1-methylethyl)-N-phenyl-, (1R,2S,5R) and cyclohexanecarboxamide, 5-methyl-2-(1-methylethyl)-N-1-naphthalenyl-(1R,2S,5R) (CAS#863091-95-6) structures with an aminoethane (CAS#75-04-7) moiety deliver a warming sensation. Both types of cyclohexanecarboxamide (cooling and warming) are efficacious at low use levels (1-10 ppm). The advantage of using such low levels of these materials allows for their formulation into higher water compositions, such as mouthrinses, without the need for additional processing aids, such as co-surfactants, oils, or other suspension agents. These materials may also provide mitigation of off tasting sensations, such as that derived from metal salts, peroxide, and CPC.

Other suitable uses for long lasting TRPM8 activity as exemplified from compound 28, would be for food applications; skin conditions, such as treatments for non-keratinized stratified epithelium; analgesic applications as pain mitigation agents; reductions in inflammation; additives to cigarettes; topical salves for muscle pain, for chronic pain from osteoarthritis, and for chemotherapy induced neuropathy; skin barrier recovery accelerants; and antipruritic or antiseptic medications; and for vasoconstriction in relaxed vessels.

The levels of use for compounds, such as compound 28, depend upon the targeted TRPM8 area of the body. For example in an oral application of a compound of the present invention, such as dentifrice, floss, chewing gum, or white strip, the levels of use may be from about 0.00001% to about 0.1%; from about 0.00005% to about 0.1%; from about 0.0001% to about 0.05%; or from about 0.001% to about 0.01% by weight of the composition. When a compound of the present invention is used in a mouthwash, the level of use may be from about 0.000001% to about 0.01% or from about 0.0001% to about 0.001% by weight of the composition. When a compound of the present invention, such as compound 28, is delivered topically, for example in shampoos and lotions the levels may be from about 0.001% to about 0.5% by weight of the composition or from about 0.01% to about 0.4% by weight of the composition.

In an oral application of a compound, for instance compound 28, such as from a dentifrice, lozenge, floss, chewing gum, or white strip, when compound 28 is split into isomers or combined, the levels of use may be from about 10% to about 70% of fraction 1 and about 10% to about 70% of fraction 2 or from about 30% to about 60% of fraction 1 and about 30% to about 60% of fraction 2. When compound 28, either isomer or combined isomers, is combined with a TRPA1 agonist, TRPV1 agonist, or both, the level of use of a TRPA1 or TRPV1 agonist would be in the range of about 0.001% to about 0.5% or from about 0.01% to about 0.2% by weight of the composition of either the TRPA1 or TRPV1 agonists, where both TRPA1 agonists and/or TRPV1 agonists may be added separately or simultaneously to the composition containing compound 28. When another TRPM8 agonist, in addition to compound 28, is used, the level of use of the additional TRPM8 agonist may be from about 0.001% to about 0.5% or from about 0.005% to about 0.3% by weight of the composition. If a TRPM8 enhancer is used, in addition to compound 28, it may be added in a range of from about 0.001% to about 0.2% or from about 0.005% to about 0.1% by weight of the composition. Compositions of the present invention may contain multiple TRPA1 and TRPV1 agonists in the ranges disclosed above to deliver the enhanced sensorial signal from compound 28.

In a topical application of a compound, such as compound 28, for example in shampoos and lotions, when compound 28 is split into isomers or combined, the levels of use may be from about 10% to about 70% of fraction 1 and about 10% to about 70% of fraction 2 or from about 30% to about 60% of fraction 1 and about 30% to about 60% of fraction 2. When compound 28, either an isomer or combined isomers, is combined with a TRPA1 and/or a TRPV1 agonist, the level of use of a TRPA1 or TRPV1 agonist may be in the range of from about 0.001% to about 0.5% or from about 0.01% to about 0.2% by weight of the composition of either of the TRPA1 or TRPV1 agonists, where both TRPA1 agonists and TRPV1 agonists may be added separately or simultaneously to the composition containing compound 28. When another TRPM8 agonist is used, in addition to compound 28, the level of use of the additional TRPM8 agonist may be from about 0.001% to about 0.5% or from about 0.005% to about 0.3% by weight of the composition. If a TRPM8 enhancer is used, in addition to compound 28, it may be used in levels of from about 0.001% to about 0.2% or from about 0.005% to about 0.1% by weight of the composition. The compositions may contain multiple TRPA1 and TRPV1 agonists in the ranges stated to deliver the enhanced sensorial signal from compound 28.

EXAMPLES

All steps as described in the EXAMPLES were conducted at room temperature unless otherwise noted.

Example 1

Achiral Separation and Characterization of Compound #28 Isomers

Compound 28 produced from a non-stereospecific synthesis was chromatographically separated to create two multi-gram fractions designated as fraction 1 and fraction 2. From the structure of compound #28, there are n=5 chiral centers, and theoretically could be $2^5$ or 32 total isomers, including 16 pairs of enantiomers. Initially, achiral chromatographic conditions were developed to separate isomers of compound 28 and characterize fractions 1 and 2 by LC-UV-MS using a Waters Acquity H Class, Ultra Performance Liquid Chromatograph (UPLC), equipped with the Sample Manager, Quaternary Solvent Manager, Tunable Ultraviolet (TUV) detector, and a QDa mass selective, single-quadrupole mass analyzer (Waters Corporation, Milford, Mass.). To prepare for analysis and characterization, a solid sample of compound 28 was weighed and dissolved at approximately 100 µg/mL in a solution consisting of 50% deionized water/50% methanol (MeOH, HPLC grade from EMD Millipore Corporation, Billerica, Mass.) and also containing 0.1% trifluoroacetic acid (TFA, Sigma Aldrich Corporation, St. Louis, Mo.).

The achiral separation of isomers contained within samples of compound 28 was achieved with a 2.1×100 mm Acquity UPLC BEH Shield RP18 column with 1.7 m particles (Waters Corporation, Milford, Mass.). A mobile phase gradient was utilized with mobile phase (A) comprising water plus 0.1% TFA from Sigma Aldrich, and mobile phase (B) comprising MeOH from EMD Millipore, Co., Billerica, Mass. The mobile phase composition was equilibrated prior to injection at 75% (A)/25% (B) and, following a 5 µl sample injection, the mobile phase composition was ramped linearly to 100% (B) at 10 minutes. 100% of mobile phase (B) was held for 3 minutes before ramping back to the original conditions in 2 minutes. A mobile phase flow rate of 0.4 ml/minute was maintained throughout the entire LC analysis method. UV traces were obtained by monitoring detector absorbance at 215 nm.

Figure 1:
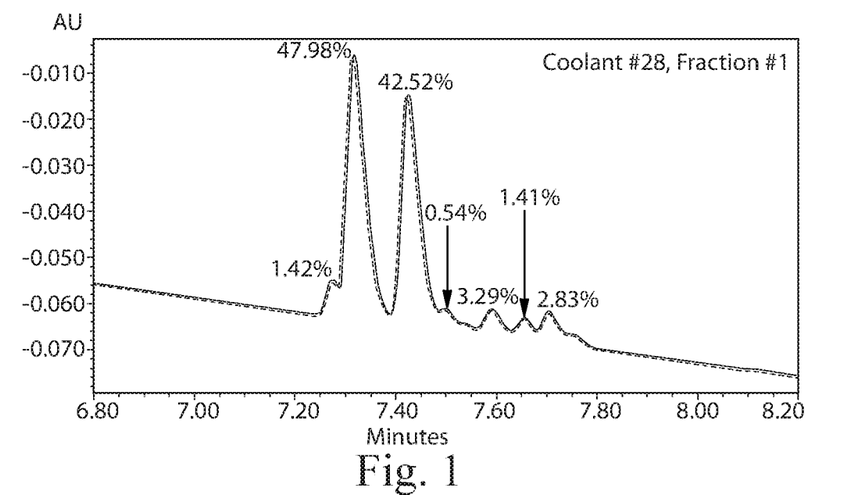
FIG. 1 UV chromatogram overlays of three replicate injections of compound 28, fraction 1. The percentages of relative peak area are shown above each isomeric compound observed within this mixture. All peaks appear at nominal m/z 374 in the QDa mass spectra, indicating that these are isomeric species.
Figure 2:
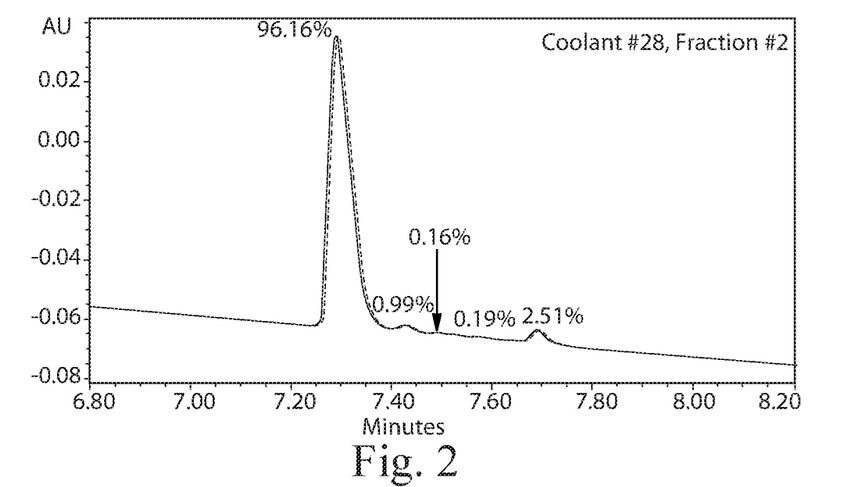
FIG. 2 UV chromatogram overlays of three replicate injections of compound 28, fraction 2. The percentages of relative peak areas are shown above for each isomeric compound observed within this mixture. All peaks appear at nominal m/z 374 in the QDa mass spectra, indicating that these are isomeric species.
Figure 3:
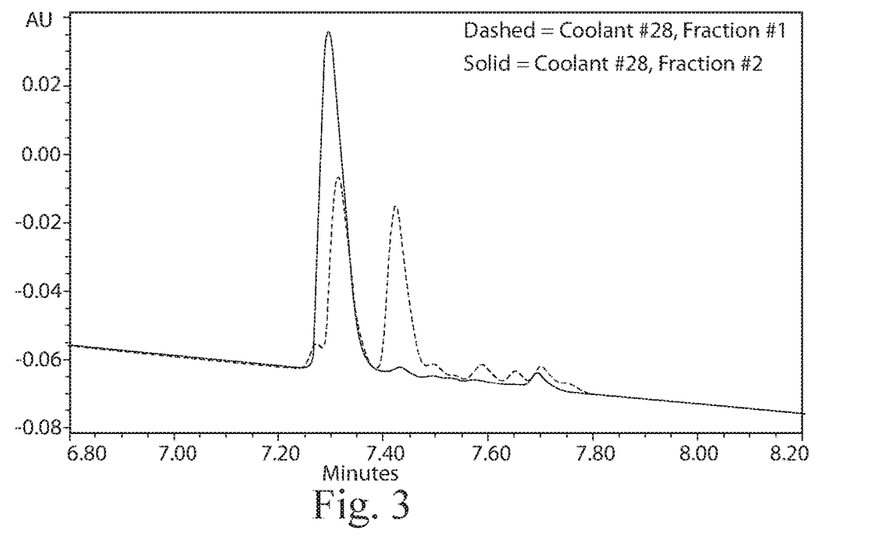
FIG. 3 UV trace overlays of chromatograms generated during separate analysis of compound 28, fraction 1 (dashed line) and fraction 2 (solid line). All peaks appear at nominal m/z 374 in the QDa mass spectra, indicating that these are isomeric species.

UV analysis of compound 28 fractions 1 and 2 are shown in FIGS. 1 and 2, respectively, indicating excellent retention time repeatability and a very good separation of the isomers found within these mixtures. FIG. 3 provides a UV overlay of a representative analysis from fraction 1 and fraction 2, highlighting the differences in isomeric composition for these two fractions of compound 28.

FIG. 3 shows the HPLC (High Performance Liquid Chromatography) separation of the isomers of compound 28. The fraction labeled fraction 1, collected at 7.4 to 7.5 minutes corresponds to the main isomer and lesser isomers that deliver the intense cooling and a low EC50 as determined from the TRPM8 activity as shown in TABLES 2, 3 and 4 below. The fraction labeled fraction 2, collected from 7.20 to 7.38 minutes corresponded to the isomers of compound 28 with much lower TRPM8 values, which did not provide a human-perceived cooling response at the dose tested as shown in TABLES 2, 3 and 4.

Figure 4:
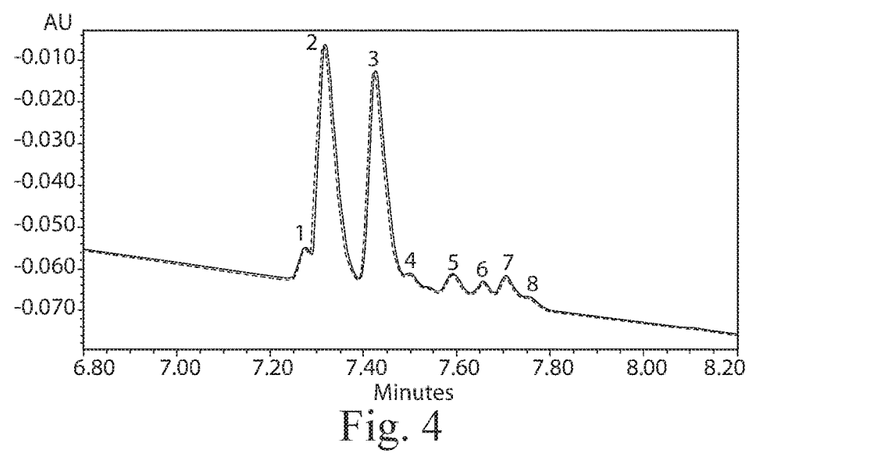
FIG. 4 UV chromatogram overlays of three replicate injections of compound 28, fraction 1. All peaks appear at nominal m/z 374 in the QDa mass spectra, indicating that these are isomeric species. The number of isomers separated from this mixture using these conditions is indicated above each peak by sequential numbering.

UV traces from analysis compound 28, fraction 1 is shown in FIG. 4, revealing 8 different isomers in this mixture separated by the achiral chromatographic conditions utilized here. QDa positive ion mass spectra of the peaks shown in FIG. 4 displayed intense protonated molecular ions at m/z 374, as expected, given the structure of compound 28, and indicating the components highlighted within FIG. 4 are isomeric species of compound 28.

Example 2

Chiral Separation and Characterization of Compound 28 Isomers Using Reversed-Phase Conditions To further improve separation of compound 28 isomers, chiral stationary phases were evaluated using reversed-phase UPLC conditions (Waters Acquity H Class, Ultra Performance Liquid Chromatograph, Waters Corporation, Milford, Mass.) with the TUV and QDa detectors described above. Waters Acquity UPC$^2$ Trefoil columns were used with UPLC or, alternately, HPLC on a Waters 2695 Separations Module, and Waters 2998 Photodiode Array Detector (both from Waters Corporation, Milford, Mass.). Both CEL1 (Cellulose tris-(3, 5-dimethylphenylcarbamate)) and AMY1 (Amylose tris-(3, 5-dimethylphenycarbamate)) (150 mm×2.1 mm with 2.5 μm particles, Waters Corporation, Milford, Mass.) Trefoil columns were evaluated for their capability to separate isomers of compound 28. Additionally, a Chiralcel OJ-R (150 mm×4.6 mm, 5 μm particles, Daicel Chemical Industries, Osaka-SHI, Japan) chiral column was evaluated. With these columns, a range of mobile phases were investigated to develop chiral separation of compound 28 isomers, including the following solvents: acetonitrile (ACN), methanol (MeOH, both from EMD Millipore, Co., Billerica, Mass.) and water (Milli-Q Millipore High Quality Water Purification System, Billerica, Mass.) with 5-25 mM levels of ammonium formate (Alfa Aesar, Ward Hill, Mass.), potassium hexafluorophosphate (KPF$_6$, TCI America, Portland, Oreg.) and/or formic acid (Sigma Aldrich, St. Louis, Mo.) and with pH ranging from 3 to 9. pH was adjusted lower with formic acid and higher with ammonium hydroxide (EMD Millipore Co., Billerica, Mass.). After more than 100 injections under various combinations of method conditions described above, no quality separation of isomers in the fraction 1 mixture of compound 28 was achieved. TABLE 1 below highlights specific conditions that were attempted without successful separation, along with reasons that these separations were determined to be unsuccessful.

TABLE 1

Examples of conditions that yielded an unsuccessful separation of compound #28 isomers with reversed phase conditions.

| Column | Mobile Phase | Reason that Separation is Unacceptable |
|---|---|---|
| CEL1 | A = Water; B = 0.1% Ammonium Formate in MeOH (gradient) | Compounds strongly retained on the column and never observed to elute |
| CEL1 | A = Water; B = 0.1% Ammonuim, Formate in 50/50 MeOH/Water, pH 9.3 (gradient) | Compounds were poorly retained and no separation was achieved |
| CEL1 | A = Water; B = 0.1% Formic Acid in 80/20 MeOH/Water, pH 7.3 (gradient) | Mixture eluted as one peak, no separation |
| AMY1 | A = Water; B = 80/20, ACN/Water (gradient) | Compounds were poorly retained and no separation was achieved |
| Chiralcel OJ-R | 70/30 Water/ACN with 50 mM KPF$_6$ (isocratic) | Only partial separation of compounds in the mixture |

TRPM8 activation was determined by measuring intracellular calcium ion ($Ca^{2+}$) level from transfected cells with the TRPM8 receptor gene, as described in CELL CULTURE PROTOCOL EXAMPLE, the results of which are shown in TABLES 2 and 3.

TABLE 2

TRPM8 Time Course Activity of compound 28

| Sample | Dose | 50 sec | 50 sec % of WS5 | 3 min | 3 min % of WS5 | 5 min | 5 min % of WS5 | 10 min | 10 min % of WS5 |
|---|---|---|---|---|---|---|---|---|---|
| Assay Buffer | na | 0.0 | 0.0 | 0.0 | 0.0 | 0.0 | 0.0 | 0.0 | 0.0 |
| WS-5 | 30 uM | 10059.7 | 100.0 | 9449.3 | 100.0 | 9468.0 | 100.0 | 9576.0 | 100.0 |
| Compound 28 fraction 1 | 100 uM | 12646.0 | 125.7 | 12520.0 | 132.5 | 12844.0 | 135.7 | 13187.0 | 137.7 |
| | 50 uM | 12419.0 | 123.5 | 12295.0 | 130.1 | 12654.0 | 133.7 | 13169.0 | 137.5 |
| | 25 uM | 13046.0 | 129.7 | 13020.0 | 137.8 | 13354.0 | 141.0 | 14341.0 | 149.8 |
| | 12.5 uM | 12430.0 | 123.6 | 12591.0 | 133.3 | 12997.0 | 137.3 | 13947.0 | 145.6 |
| | 6.25 uM | 12229.0 | 121.6 | 12775.0 | 135.2 | 13098.0 | 138.3 | 14102.0 | 147.3 |
| | 3.125 uM | 11637.0 | 115.7 | 12602.0 | 133.4 | 12939.0 | 136.7 | 13850.0 | 144.6 |
| | 1.563 uM | 11114.0 | 110.5 | 12135.0 | 128.4 | 12499.0 | 132.0 | 13440.0 | 140.4 |
| | 781 nM | 9786.0 | 97.3 | 12182.0 | 128.9 | 12618.0 | 133.3 | 13661.0 | 142.7 |
| | 390 nM | 7592.0 | 75.5 | 11373.0 | 120.4 | 11968.0 | 126.4 | 13121.0 | 137.0 |
| | 195 nM | 5418.0 | 53.9 | 11037.0 | 116.8 | 11824.0 | 124.9 | 13046.0 | 136.2 |
| | 97.6 nM | 3963.0 | 39.4 | 9744.0 | 103.1 | 10711.0 | 113.1 | 12011.0 | 125.4 |
| | 48.8 nM | 2916.0 | 29.0 | 8017.0 | 84.8 | 8983.0 | 94.9 | 10224.0 | 106.8 |
| | 24.4 nM | 1936.0 | 19.2 | 6405.0 | 67.8 | 7593.0 | 80.2 | 8879.0 | 92.7 |
| | 12.2 nM | 3018.0 | 30.0 | 8783.0 | 93.0 | 9830.0 | 103.8 | 11065.0 | 115.5 |
| | 6.1 nM | 884.0 | 8.8 | 3452.0 | 36.5 | 4426.0 | 46.7 | 5375.0 | 56.1 |

TABLE 3

TRPM8 Time Course Activity of Isomer of compound 28

| Sample | Dose | 50 sec | 50 sec % of WS5 | 3 min | 3 min % of WS5 | 5 min | 5 min % of WS5 | 10 min | 10 min % of WS5 |
|---|---|---|---|---|---|---|---|---|---|
| Assay Buffer | na | 0.0 | 0.0 | 0.0 | 0.0 | 0.0 | 0.0 | 0.0 | 0.0 |
| WS-5 | 30 uM | 10059.7 | 100.0 | 9449.3 | 100.0 | 9468.0 | 100.0 | 9576.0 | 100.0 |
| Compound 28 fraction 2 | 100 uM | 12246.0 | 121.7 | 11826.0 | 125.2 | 12074.0 | 127.5 | 12287.0 | 128.3 |
| | 50 uM | 12648.0 | 125.7 | 12352.0 | 130.7 | 12644.0 | 133.5 | 13179.0 | 137.6 |
| | 25 uM | 12110.0 | 120.4 | 11993.0 | 126.9 | 12284.0 | 129.7 | 13140.0 | 137.2 |
| | 12.5 uM | 12415.0 | 123.4 | 12501.0 | 132.3 | 12801.0 | 135.2 | 13755.0 | 143.6 |
| | 6.25 uM | 12236.0 | 121.6 | 12644.0 | 133.8 | 12891.0 | 136.2 | 13793.0 | 144.0 |
| | 3.125 uM | 11757.0 | 116.9 | 12699.0 | 134.4 | 12937.0 | 136.6 | 13890.0 | 145.1 |
| | 1.563 uM | 11331.0 | 112.6 | 12663.0 | 134.0 | 12954.0 | 136.8 | 13892.0 | 145.1 |
| | 781 nM | 10428.0 | 103.7 | 12887.0 | 136.4 | 13091.0 | 138.3 | 14116.0 | 147.4 |
| | 390 nM | 8766.0 | 87.1 | 11955.0 | 126.5 | 12301.0 | 129.9 | 13026.0 | 136.0 |
| | 195 nM | 7287.0 | 72.4 | 11477.0 | 121.5 | 12007.0 | 126.8 | 12427.0 | 129.8 |
| | 97.6 nM | 5007.0 | 49.8 | 10101.0 | 106.9 | 10747.0 | 113.5 | 11375.0 | 118.8 |
| | 48.8 nM | 2502.0 | 24.9 | 7721.0 | 81.7 | 8488.0 | 89.6 | 9289.0 | 97.0 |
| | 24.4 nM | 2311.0 | 23.0 | 6441.0 | 68.2 | 7226.0 | 76.3 | 7848.0 | 82.0 |
| | 12.2 nM | 1814.0 | 18.0 | 5446.0 | 57.6 | 6224.0 | 65.7 | 6809.0 | 71.1 |
| | 6.1 nM | 1944.0 | 19.3 | 4350.0 | 46.0 | 4763.0 | 50.3 | 4844.0 | 50.6 |

The TRPM8 data shown in TABLES 2 and 3, where TABLE 2 corresponds to fraction 1 and TABLE 3 corresponds to fraction 2, compares the dose response of the two HPLC separations, of the isomers (fraction 1, fraction 2) of compound 28. As shown in TABLES 2 and 3, both fractions activate TRPM8 rapidly at 781 nM of each. However, fraction 1 continued to activate at lower and lower doses compared to fraction 2. Fraction 1 was 103.8% of the control at 5 minutes of activation from a 12.2 nM dose; whereas, fraction 2 at the same time point and dose was 65.7% of the control. At 10 minutes of activation, the 12.2 nM dose was 115.5% of the control for fraction 1 and 71.1% of the control for fraction 2. The reading at 12.2 nM for fraction one was abnormally high and considered an outlier data point. If included, the 12.2 nM data point would make the EC50 lower than realistically possible and was therefore excluded from the EC50 calculations in TABLE 3. These differences in isomers were further illustrated in the EC50 values as shown in TABLE 4 below.

TABLE 4

EC50 Calculation of Isomer fractions

| | EC50 in TRPM8 (µM) | | | |
|---|---|---|---|---|
| | 50 sec | 3 min | 5 min | 10 min |
| fraction 2 | 0.1972 | 0.05548 | 0.04567 | 0.0374 |
| fraction 1 | 0.2848 | 0.03173 | 0.02500 | 0.02423 |

Example 3

Cell Culture Protocol

To determine what effect, if any, test compounds had on TRPM8 (SEQ ID NO: 1) activation the protocols listed below were used.

TRPM8 Protocol-FLIPR Assay

To determine whether TRPM8 is activated, the intracellular calcium ion ($Ca^{2+}$) level was measured from transfected cells with the TRPM8 receptor sequence (SEQ ID NO: 1). HEK-293 (human embryonic kidney) cells stably transfected with human TRPM8 were grown in 15 ml growth medium (high glucose DMEM (Dulbecco's Modification of Eagle's Medium) supplemented with 10% FBS (fetal bovine serum), 100 ug/ml penicillin/streptomycin, 5 µg/ml blasticindin, and 100 µg/ml zeocin) in a 75 $cm^2$ flask for 3 days at 37° C. in a mammalian cell culture incubator set at 5% $CO_2$. Cells were detached with addition of 2 ml of trypsin-EDTA buffer (GIBCO® 25200, Invitrogen, Grand Island, N.Y.) for about 2-3 min. Trypsin was inactivated by addition of 8 ml growth medium. Cells were transferred to a 50 ml tube and centrifuged at 850 rpm for 3 minutes to remove medium. After centrifugation, a pellet of cells was formed in the bottom of the tube separating them from the supernatant solution. The supernatant was discarded and the cell pellet was suspended in 1 ml of fresh growth medium to which 5 µl (12.5 µg) of Fluo-4 AM (Molecular Probes, Inc., Eugene, Oreg.) calcium indicator was added and incubated for 30 min with gentle shaking. Fluo-4 AM is a fluorescent dye used for quantifying cellular $Ca^{2+}$ concentrations in the 100 nM to 1 microM range. At the end of 30 minutes, 45 ml of assay buffer (1×HBSS (Hank's Balanced Salt Solution), 20 mM HEPES (4-(2-Hydroxyethyl)-1-piperazineethanesulfonic acid)) was added to wash cells and the resulting mixture was then centrifuged at 850 rpm for 3 minutes to remove excess buffer and Fluo-4 AM calcium indicator.

The pelleted cells were re-suspended in 10 ml assay buffer and 90 al aliquots (~50,000 cells) per well delivered to a 96-well assay plate containing 10 al of test compounds (1 mM in assay buffer, final concentration 100 µM) or buffer control and incubated at room temperature for 30 minutes. After 30 minutes, a plate was placed into a fluorometric imaging plate reader (FLIPR TETRA from Molecular Devices, Sunnyvale, Calif.) and basal fluorescence recorded (excitation wave length 488 nm and emission wave length 510 nm). Then 20 µl of 180 µM solution of TRPM8 agonist WS5 coolant was added to the assay buffer and the fluorescence signals were automatically recorded by FLIPR. For determining the direct effect of test compounds on TRPM8, fluorescence was measured immediately after addition of each compound (TABLES 2 and 3). Additional discussion of the FLIPR method can be found in Smart et al., Characterization using FLIPR of human vanilloid VR1 receptor pharmacology, European Journal of Pharmacology 417, 51-58 (2001) and Liu et al., Development and validation of a platelet calcium flux assay using a fluorescent imaging plate reader, Analytical Biochemistry 357, 216-224 (2006).

Example 4

Chiral Separation and Characterization of Compound 28 Isomers Using Supercritical Fluid Chromatographic Conditions With the difficulties in developing an effective chiral separation of compound 28 isomers using reversed-phase conditions, supercritical fluid chromatography (SFC) was evaluated for its potential to deliver a comprehensive separation of compound 28 isomers. For the supercritical fluid chiral separation method development, a Waters Ultra Performance Convergence Chromatograph (UPC2, Waters Corporation, Milford, Mass.) was combined with an Applied Biosystems API 4000 triple quadrupole mass spectrometer (Applied Biosystems, Toronto, Canada).

Amylose tris [(S)-α-methylbenzylcarbamate] (AS-H), Amylose tris (3,5-dimethylphenylcarbamate) (AD-H), Cellulose 3,5-dimethylphenylcarbamate (OD-H), Cellulose tris (methyl benzoate) (OJ-H), stationary phases (all 250 mm×4.6 mm, 5 μm particles, Chiral Technologies Inc., West Chester, Pa.) and Cellulose tris-(3-chloro-4-methylphenylcarbamate) (150 mm×3 mm, 2.5 μm particles, Waters Corporation, Milford, Mass.) stationary phases were evaluated along with supercritical fluid mobile phases consisting of combinations of high pressure carbon dioxide (Matheson, Coleman Instrument grade, Matheson Tri-Gas, Inc., Basking Ridge, N.J.), methanol (LC-MS grade, Fisher Scientific, Pittsburgh, Pa.), isopropanol (LC-MS grade, Fisher Scientific, Pittsburgh, Pa.), and ethanol (HPLC Gradient grade, Merck & Co., Inc., Kenilworth, N.J.) along with additives, such as ammonium acetate (LC-MS grade, Fisher Scientific, Pittsburgh, Pa.) triethylamine (LC-MS grade, Sigma Aldrich Corporation, St. Louis, Mo.), and formic acid (LC-MS grade, Sigma Aldrich Corporation, St. Louis, Mo.). Detection was achieved with the API 4000 triple quadrupole mass spectrometer operated in positive ionization atmospheric pressure chemical ionization (+APCI), selected reaction monitoring (SRM) mode and continuously recording response from the m/z 374 to 83 transition. Collisional activation was achieved in the second quadrupole with collision energy of 47 eV, collision exit potential of 5 V, declustering potential of 120 V, source temperature of 500° C., needle current of 3, and collision gas pressure of 5 with nitrogen target gas.

Overall, more than 100 different combinations of SFC conditions were attempted without achieving a successful SFC separation of compound 28 isomers. Reasons for unacceptable separations were the same as listed for the reversed phase chiral separation on TABLE 1, and included inadequate retention of compound 28 isomers, inability to elute compound 28 isomers from the column, and/or inability to achieve good separation of isomers that were adequately retained and eluted.

Effective chiral separation of compound 28 isomers is clearly very challenging and is not obvious, especially given its multiple functionalities, five chiral centers, and 32 isomeric possibilities. After the extensive investigations outlined above and followed by strategic optimization, it was finally discovered that a Chiralpak AS-H and Chiralpak AD-H column when combined, in series in the order of AS-H follow by AD-H, with an optimized mobile phase, were able to successfully separate all isomers of compound 28 produced to date. It should be noted that AD-H is meant to include any column with Amylose tris (3,5-dimethylphenylcarbamate) chemistry and AS-H includes any column with Amylose tris [(S)-α-methylbenzylcarbamate] chemistry. Likewise, any other column chemistries specified within refer to all columns that include these respective chemistries, and not just one specific type of column manufactured by a specific supplier.

For the successful chiral separation, the Chiralpak AS-H column was followed with a Chiralpak AD-H column with a mobile phase consisting of carbon dioxide, ethanol, and 20 mM ammonium acetate. A gradient separation was performed by injecting the sample mixture into the mobile phase containing 10% ethanol (with 20 mM ammonium acetate) in a supercritical fluid stream of pressurized $CO_2$ [150 bar backpressure] with a flow rate of 1.0 ml/min at a column temperature held constant at 40° C. The percent of ethanol was ramped linearly at 0.25% per minute to a maximum of 26% before returning to initial conditions. Prior to injection, samples were dissolved in methyl tert butyl ether and 7.5 μL were injected. Detection was achieved with the API 4000 triple quadrupole by monitoring the SRM transition of m/z 374 to 83 under the conditions described above.

TABLE 5

Figure 5:
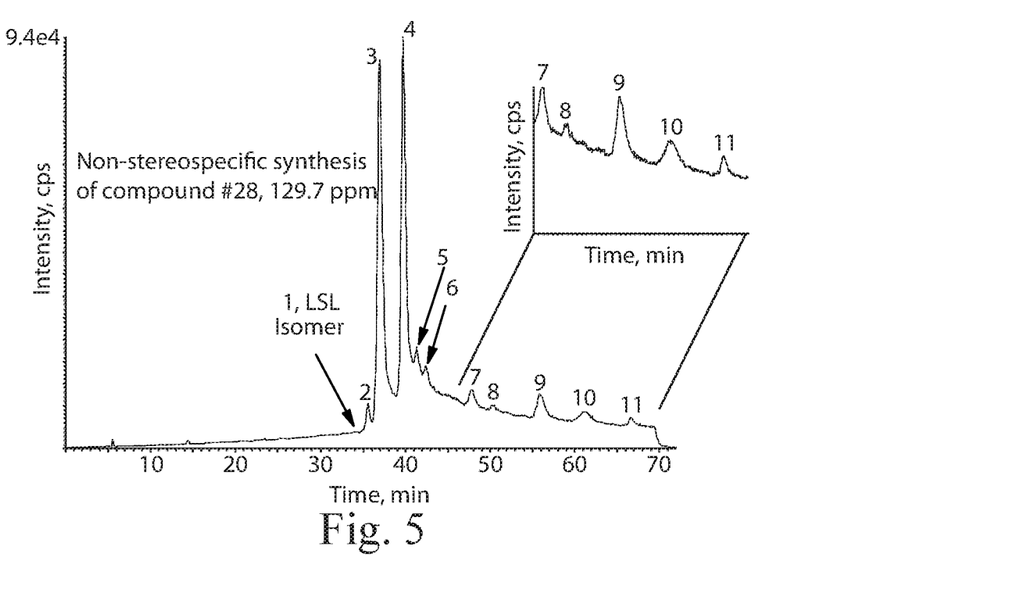
FIG. 5 Chiral SFC separation of compound 28 isomers found in fraction 1 produced via non-stereospecific synthesis. The same chiral SFC chromatographic separation conditions were also used for analysis of reaction products from the stereoselective synthesis of the compound 28 DSL, DRL, and LSL isomers. The SFC results from the analysis of stereoselective reaction products show a contrasting very high isomeric purity (99+%), as indicated on TABLE 5.

Compound 28 isomeric content within synthetic mixtures, as determined by chiral SFC chromatographic analysis of materials produced by non-stereospecific and stereospecific synthetic routes. Isomers with a peak area of >0.5% of the total are included on this TABLE and labeled in FIG 5.

| | | % of Total Peak Area Per Sample | | | |
|---|---|---|---|---|---|
| Compound 28 Isomer | Retention Time (min) | Non-Stereospecific Synthesis | DSL Stereospecific Synthesis | DRL Stereospecific Synthesis | LSL Stereospecific Synthesis |
| 1 | 34.0 | 0 | 0 | 0 | 100 |
| 2 | 35.6 | 2 | 0 | 0 | 0 |
| 3 | 37.0 | 43 | 99 | 0 | 0 |
| 4 | 39.8 | 43 | 0 | 99 | 0 |
| 5 | 41.4 | 3 | 0 | 0 | 0 |
| 6 | 42.4 | 2 | 0 | 0 | 0 |
| 7 | 47.7 | 2 | 0 | 0 | 0 |
| 8 | 50.5 | 1 | 0 | 0 | 0 |
| 9 | 55.9 | 3 | 0 | 0 | 0 |
| 10 | 61.1 | 1 | 0 | 0 | 0 |
| 11 | 66.7 | 1 | 0 | 0 | 0 |

In addition to stereoselective synthesis, a quality chromatographic purification is an alternate approach for isolating high-purity, single isomers of compound 28. We have discovered that chiral selectors AD-H and AS-H, when used in series along with an optimal mobile phase, can produce a successful separation of these isomeric compounds that would be very useful for isomeric purification. Chiral separation of compound 28 isomers is very difficult and is not obvious, given its complex functionality, five chiral centers, and 32 possible isomers. Via strategic optimization and development, a unique separation has been developed based on a combination of AD-H and AS-H chiral selectors. Optimal use of amylose-based, chiral stationary phases in combination with subcritical, supercritical, or enhanced fluidity alcohol/$CO_2$ mobile phases are expected to provide good separations of compound 28 isomers. For the purposes of compound 28 isomeric purification, it is desirable to limit the use of any non-volatile or semi-volatile additives to facilitate removal of the mobile phase upon collection of the purified compound 28 isomers. For example, in certain embodiments the mobile phase may comprise less than about 0.2% non-volatile additive or semi-volatile additive (such as ammonium acetate) by weight of the mobile phase. Additionally, use of two or more successive stages of a quality separation may also be utilized to increase purity of each isomeric fraction, as required for a given application.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm."

Every document cited herein, including any cross referenced or related patent or application and any patent application or patent to which this application claims priority or benefit thereof, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

---

What is claimed is:

1. A method of separating specific stereoisomers using supercritical fluid chromatography comprising:
   a. providing a column with Amylose tris [(S)-α-methylbenzylcarbamate] (AS-H);
   b. providing a column with Amylose tris (3,5-dimethylphenylcarbamate) (AD-H);
   c. providing compound 28 having the below formula and wherein $R_1$ is $CH_3$ wherein compound 28 is run through the AS-H column and then run through the AD-H column to separate stereoisomers.

2. The method of claim 1, wherein the AD-H column comprises a mobile phase including carbon dioxide, ethanol, and ammonium acetate.

3. The method of claim 2, wherein the ammonium acetate is 0-50 mM.

4. The method of claim 1, wherein the separation is achieved with amylose-based, chiral stationary phases used with at least one of: supercritical fluidity stream of pressurized $CO_2$, subcritical fluidity stream of pressurized $CO_2$ or enhanced fluidity stream of pressurized $CO_2$.

5. The method of claim 1, wherein the AS-H column is used in combination with a mobile phase comprising at least one of: of carbon dioxide, alcohol, or ammonium acetate.

6. The method of claim 5, wherein the alcohol is ethanol.

7. The method of claim 1, wherein the AD-H column is used in combination with a mobile phase comprising at least one of: of carbon dioxide, alcohol, or ammonium acetate.

8. The method of claim 7, wherein the alcohol is ethanol.

9. The method of claim 1, wherein the AS-H column is used in combination with a gradient separation comprising at least one of supercritical fluidity stream of pressurized $CO_2$, subcritical fluidity stream of pressurized $CO_2$ or enhanced fluidity stream of pressurized $CO_2$.

10. The method of claim 1, wherein the AD-H column is used in combination with a gradient separation comprising at least one of supercritical fluidity stream of pressurized $CO_2$, subcritical fluidity stream of pressurized $CO_2$ or enhanced fluidity stream of pressurized $CO_2$.

11. The method of claim 2, wherein the mobile phase comprises less than about 0.2% non-volatile additive or semi-volatile additive by weight of the mobile phase.

12. The method of claim 11, wherein the mobile phase comprises less than about 0.2% ammonium acetate.

13. The method of claim 1, wherein an isolated stereoisomer has a purity of at least about 70%.

14. The method of claim 13, wherein the isolated stereoisomer has a purity of at least about 85%.

15. The method of claim 14, wherein the isolated stereoisomer has a purity of at least about 95%.

16. The method of claim 15, wherein the isolated stereoisomer has a purity of at least about 99%.

* * * * *

SEQUENCE LISTING

```
<160> NUMBER OF SEQ ID NOS: 1

<210> SEQ ID NO 1
<211> LENGTH: 3315
<212> TYPE: DNA
<213> ORGANISM: Homo sapiens

<400> SEQUENCE: 1
atgtccttcg agggagccag gctcagcatg aggagccgca gaaatggtac tatgggcagc      60
acccggaccc tgtactccag tgtatctcgg agcacagacg tgtcctacag tgacagtgat     120
ttggtgaatt ttattcaggc aaattttaaa aaacgagaat gtgtcttctt taccagagac     180
tccaaggcca tggagaacat atgcaagtgt ggttatgccc agagccagca catcgaaggc     240
acccagatca accaaaatga gaagtggaac tacaaaaaac ataccaagga gtttccaaca     300
gacgccttcg gggacattca gtttgagact ctggggaaga aaggcaagta cttacgcttg     360
tcctgtgaca ccgactctga aactctctac gaactgctga cccagcactg gcaccctcaaa    420 acacccaacc tggtcatttc agtgacgggt ggagccaaaa actttgcttt gaagccacgc     480
atgcgcaaga tcttcagcag gctgatttac atcgcacagt ctaaaggtgc gtggattctc     540
actggaggca ctcactacgg cctgatgaag tacataggcg aggtggtgag agacaacacc     600
atcagcagga actcagaaga gaacatcgtg gccattggca tcgcagcatg gggcatggtc     660
tccaacaggg acaccctcat caggagctgt gatgatgagg acattttttc agctcaatac     720
atcatggatg actttaccag agaccctcta tacatcctgg acaacaacca tacccacctg     780
ctgcttgtgg acaacggttg tcatggacac cccacagtgg aagccaagct ccggaatcag     840
ctggaaaagt acatctctga gcgcaccagt caagattcca actatggtgg taagatcccc     900
atcgtgtgtt tgcccaagg aggtggaaga gagactctaa aagccatcaa cacctctgtc     960
aaaagcaaga tcccttgtgt ggtggtggaa ggctcggggc agattgctga tgtgatcgcc    1020
```

```
agcctggtgg aggtggagga tgttttaacc tcttccatgg tcaaagagaa gctggtacgc    1080 ttttaccac gcactgtgtc ccggctgcct gaagaggaaa ttgagagctg atcaaatgg      1140 ctcaaagaaa ttcttgagag ttctcaccta ctcacagtaa ttaagatgga agaggctgga    1200
gatgagattg tgagcaacgc catttcctat gcgctgtaca aagccttcag cactaatgag    1260
caagacaagg acaactggaa tggacagctg aagcttctgc tggagtggaa ccagttggac    1320
cttgccagtg atgagatctt caccaatgat cgccgctggg agtctgccga ccttcaggag    1380
gtcatgttca cggctctcat aaaggacaga cccaagtttg tccgcctctt tctggagaat    1440
ggcctgaatc tgcagaagtt tctcaccaat gaagtcctca cagagctctt ctccacccac    1500
ttcagcaccc tagtgtaccg aatctgcag atcgccaaga actcctacaa tgacgcactc     1560
ctcacctttg tctggaagtt ggtggcaaac ttccgtcgaa gcttctggaa agaggacaga    1620
agcagcaggg aggacttgga tgtggaactc catgatgcat ctctcaccac ccggcacccg    1680
ctgcaagctc tcttcatctg gccattctt cagaacaaga aggaactctc caaggtcatt     1740
tgggagcaga ccaaaggctg tactctggca gccttggggg ccagcaagct tctgaagacc    1800
ctggccaaag ttaagaatga tatcaacgct gctggggaat cggaggaact ggccaatgaa    1860
tatgagaccc gagcagtgga gttgttcacc gagtgttaca gcaatgatga agacttggca    1920
gaacagctac tggtctactc ctgcgaagcc tggggtggga gcaactgtct ggagctggca    1980
gtggaggcta cagatcagca tttcatcgct cagcctgggg tccagaatt cctttctaag     2040 caatggtatg gagagatttc ccgagacacg aagaactgga agattatcct gtgtctattc    2100
atcatcccct tagtgggctg tggcctcgta tcatttagga agaaacccat tgacaagcac    2160
aagaagctgc tgtggtacta tgtggccttc ttcacgtcgc ccttcgtggt cttctcctgg    2220 aacgtgtct tctacatcgc cttcctcctg ctgtttgcct atgtgctgct catggacttc     2280
cactcagtgc acacacccc cgagctgatc tctacgccc tggtcttcgt cctcttctgt      2340
gatgaagtga ggcagtggta catgaacgga gtgaattatt tcaccgacct atggaacgtt    2400
atggacaccc tgggactctt ctacttcata gcgggtattg tattccggct ccactcttct    2460
aataaaagct cgttgtactc tgggcgcgtc attttctgtc tggattacat tatattcacg    2520
ctaaggctca tccacatttt caccgtcagc aggaacttgg acccaagat tataatgctg     2580 cagcggatgc tgatcgacgt tttcttcttc ctgttcctct tgctgtgtg gatggtggcc     2640 tttggcgtgg ccagacaggg gatcctaagg caaaatgaac agcgctggag atggatcttc    2700
cgctctgtca tctatgagcc ctacctggcc atgtttggcc aggttcccag tgacgtggat    2760
agtaccacat atgacttctc ccactgtacc ttctcgggaa atgagtccaa gccactgtgt    2820
gtggagctgg atgagcacaa cctgcccgc ttccctgagt ggatcaccat tccgctggtg     2880
tgcatctaca tgctctccac caatatcctt ctggtcaacc tcctggtcgc catgtttggc    2940
tacacggtag gcattgtaca ggagaacaac gaccaggtct ggaaattcca gcggtacttc    3000
ctggtgcagg agtactgcaa ccgcctaaac atccccttcc ccttcgttgt cttcgcttat    3060
ttctacatgg tggtgaagaa gtgtttcaaa tgctgctgta aagagaagaa tatggagtct    3120
aatgcctgct gtttcagaaa tgaggacaat gagactttgg cgtgggaggg tgtcatgaag    3180
gagaattacc ttgtcaagat caacacgaaa gccaacgaca actcagagga gatgaggcat    3240
cggtttagac aactggactc aaagcttaac gacctcaaaa gtcttctgaa agagattgct    3300
aataacatca agtaa                                                     3315
```